(12) United States Patent
Di Bacco et al.

(10) Patent No.: US 11,268,154 B2
(45) Date of Patent: Mar. 8, 2022

(54) METHODS FOR THE IDENTIFICATION, EVALUATION AND TREATMENT OF PATIENTS HAVING MULTIPLE MYELOMA

(71) Applicants: Millennium Pharmaceuticals, Inc., Cambridge, MA (US); Celgene Corporation, Summit, NJ (US)

(72) Inventors: Alessandra M. Di Bacco, Cambridge, MA (US); George J. Mulligan, Cambridge, MA (US)

(73) Assignee: Takeda Pharmaceutical Company Limited

( * ) Notice: Subject to any disclaimer, the term of this patent is extended or adjusted under 35 U.S.C. 154(b) by 287 days.

(21) Appl. No.: 15/772,954

(22) PCT Filed: Nov. 4, 2016

(86) PCT No.: PCT/US2016/060552
§ 371 (c)(1),
(2) Date: May 2, 2018

(87) PCT Pub. No.: WO2017/079572
PCT Pub. Date: May 11, 2017

(65) Prior Publication Data
US 2018/0320236 A1    Nov. 8, 2018

Related U.S. Application Data

(60) Provisional application No. 62/334,172, filed on May 10, 2016, provisional application No. 62/276,645, filed on Jan. 8, 2016, provisional application No. 62/265,768, filed on Dec. 10, 2015, provisional application No. 62/263,261, filed on Dec. 4, 2015, provisional application No. 62/250,844, filed on Nov. 4, 2015.

(51) Int. Cl.
| | | |
|---|---|---|
| *C12Q 1/68* | (2018.01) | |
| *C12Q 1/6886* | (2018.01) | |
| *G01N 33/50* | (2006.01) | |
| *G01N 33/574* | (2006.01) | |
| *A61K 31/454* | (2006.01) | |
| *A61K 31/573* | (2006.01) | |
| *A61K 31/69* | (2006.01) | |
| *A61P 35/00* | (2006.01) | |
| *A61K 9/48* | (2006.01) | |

(52) U.S. Cl.
CPC ....... *C12Q 1/6886* (2013.01); *G01N 33/5091* (2013.01); *G01N 33/57426* (2013.01); *A61K 9/485* (2013.01); *A61K 9/4858* (2013.01); *A61K 9/4866* (2013.01); *A61K 31/454* (2013.01); *A61K 31/573* (2013.01); *A61K 31/69* (2013.01); *A61P 35/00* (2018.01); *C12Q 2600/106* (2013.01); *C12Q 2600/156* (2013.01)

(58) Field of Classification Search
None
See application file for complete search history.

(56) References Cited

U.S. PATENT DOCUMENTS 7,687,662 B2 * 3/2010 Olhava ................ A61K 31/198
562/7

FOREIGN PATENT DOCUMENTS

| WO | 2012149419 A1 | 11/2012 |
|---|---|---|
| WO | 2015179443 A1 | 11/2015 |

OTHER PUBLICATIONS

Shin et al; International Journal of Laboratory Hematology, vol. 34, pp. 541-546, 2012.*
Avet-Loiseau, H., et al., "Impact of Cytogenetic Risk Status on Efficacy and Safety of Ixazomib-Lenalidomide-Dexamethasone (IRD) Vs Placebo-RD in Relapsed/Refractory Multiple Myeloma Patients in the Global TOURMALINE-MM1 Study", Haematologica, The Hematology Journal : Official Organ of the European Hematology Association, Fondazione Ferrata Storti, IT, vol. 101, No. Suppl.1, Jun. 1, 2016, p. 80.
ClinicalTrials.gov: "A Phase 3 Study Comparing Oral Ixazomib Plus Lenalidomide and Dexamethasone Versus Placebo Plus Lenalidomide and Dexamethasone in Adult Patients With Relapsed and/or Refractory Multiple Myeloma", Aug. 4, 2015.
ClinicalTrials.gov: "A Phase 3 Study Comparing Oral Ixazomib Plus Lenalidomide and Dexamethasone Versus Placebo Plus Lenalidomide and Dexamethasone in Adult Patients With Relapsed and/or Refractory Multiple Myeloma", May 3, 2016.
Kumar, S.K., et al., "Weekly MLN9708, an investigational oral proteasome inhibitor, in relapsed/refractory multiple myeloma: Results from a phase I study after full enrollment", ASCO Annual Meeting 2013, Jun. 1, 2013.

(Continued)

*Primary Examiner* — Jehanne S Sitton
(74) *Attorney, Agent, or Firm* — Honigman LLP; Lucy X. Yang; Jonathan P. O'Brien

(57) ABSTRACT

The present disclosure relates to methods for the treatment of multiple myeloma in patients who have one or more cytogenetic alterations. In particular, the disclosure provides methods for treatment of multiple myeloma in patients who have one or more cytogenetic alternations by administering to a patient a treatment regimen comprising a proteasome inhibitor or a pharmaceutically acceptable salt, stereoisomeric or tautomeric form thereof if said patient is identified as a likely responder to the treatment regimen by assessing the presence of said cytogenetic alterations.

19 Claims, No Drawings

(56) References Cited

OTHER PUBLICATIONS

Kumar, S.K., et al., "Safety and tolerability of ixazomib, an oral proteasome inhibitor, in combination with lenalidomide and dexamethasone in patients with previously untreated multiple myeloma: an open-label phase 1/2 study", The Lancet Oncology, vol. 15, No. 13, Dec. 1, 2014, pp. 1503-1512.

Lu, G., et al., "Plasma Cell Enrichment Enhances Detection of High-Risk Cytogenomic Abnormalities by Fluorescence In Situ Hybridization and Improves Risk Stratification of Patients With Plasma Cell Neoplasms", Archives of Pathology & Laboratory Medicine, vol. 137, No. 5, May 1, 2013, pp. 625-631.

Moreau, P., et al., "Oral Ixazomib, Lenalidomide, and Dexamethasone for Multiple Myeloma", The New England journal of medicine, Apr. 28, 2016, pp. 1621-1633.

* cited by examiner

METHODS FOR THE IDENTIFICATION, EVALUATION AND TREATMENT OF PATIENTS HAVING MULTIPLE MYELOMA

RELATED APPLICATIONS

This application is a 35 U.S.C. § 371 United States National Phase Application of, and claims priority to, PCT Application No. PCT/US2016/060552, filed Nov. 4, 2016, which claims the benefit under 35 U.S.C. § 119 of U.S. Provisional Application Ser. No. 62/250,844, filed Nov. 4, 2015, U.S. Provisional Application Ser. No. 62/263,261, filed Dec. 4, 2015, U.S. Provisional Application Ser. No. 62/265,768, filed Dec. 10, 2015, U.S. Provisional Application Ser. No. 62/276,645, filed Jan. 8, 2016, and U.S. Provisional Application Ser. No. 62/334,172, filed May 10, 2016. The entire contents of the foregoing applications are incorporated herein by reference in their entireties.

FIELD

The present disclosure relates to methods for the treatment of multiple myeloma in patients who have one or more cytogenetic alterations. In particular, the disclosure provides methods for treatment of multiple myeloma in patients who have one or more cytogenetic alterations by administering to a patient a treatment regimen comprising a proteasome inhibitor or a pharmaceutically acceptable salt, stereoisomeric or tautomeric form thereof, if said patient is identified as a likely responder to the treatment regimen by assessing the presence of said cytogenetic alterations.

BACKGROUND

Multiple myeloma, a B-cell tumor of malignant plasma cells within the bone marrow, remains incurable despite advances in novel therapies with proteasome inhibitors (PIs), immunomodulating drugs, and stem cell transplant (SCT) therapy. Multiple myeloma is characterized by the accumulation of plasma cells in the bone marrow (and other organs) and can result in bone marrow failure, bone destruction, hypercalcemia, and renal failure. It constitutes approximately 1% of all reported neoplasms and approximately 13% of hematologic cancers worldwide. In the Americas, Canada, and Western European countries, approximately five to seven new cases of multiple myeloma are diagnosed per 100,000 people each year. Palumbo and Anderson, *N Engl J Med* 2011; 364(11):1046-60; Landgren and Weiss, *Leukemia* 2009; 23(10):1691-7; Harousseau, et al., *Annals of Oncology* 2008; 19 Suppl 2:ii55-7. Although less common in Asian countries, incidences of multiple myeloma have increased almost 4-fold in the past 25 years and are characterized by younger age of onset, more invasive disease, and a less favorable prognosis (Huang, et al., Cancer 2007; 110(4):896-905; Qiu, et al., Clinical Epidemiological Study on Multiple Myeloma in China (ASH Annual Meeting Abstracts) 2008; 112(11):abstr 2723).

Multiple myeloma is sensitive to many cytotoxic drugs including alkylating agents, anthracyclines, and corticosteroids for both initial treatment and relapsed disease. Over the past decade, significant achievements have been made in expanding treatment options for multiple myeloma with novel therapies such as thalidomide, bortezomib, and lenalidomide. These regimens have extended progression-free survival (PFS) and/or time-to-progression (TTP) (Palumbo, et al., Leukemia 2008; 22(2):414-23; Mateos, et al., Journal of Clinical Oncology 2010; 28(13):2259-66; Gay, et al., Haematologica 2010; 94:0507; Richardson, et al., Hematology 2007:317-23; Dimopoulos, et al., Leukemia 2009; 23(11):2147-52). The introduction of novel therapies and the increased use of high-dose therapy (HDT) significantly improved overall survival in patients with newly diagnosed multiple myeloma (NDMM) who were eligible for autologous stem cell transplant (ASCT) (Kumar, et al., Blood 2008; 111(5):2516-20; Brenner, et al., Blood 2008; 111(5):2521-6; Libby, et al., Declining myeloma mortality rates in the United States following introduction of novel therapies In: International Myeloma Workshop Paris, France; 2011).

Despite more therapeutic options, multiple myeloma remains incurable, and patients with early stage cancer remain at risk for relapse after their initial therapy. When patients relapse after their initial therapy, they demonstrate variable responses to subsequent treatments with decreasing likelihood and duration of response (DOR). Patients become refractory to approved therapies and ultimately are left with no alternative treatment options. Importantly, the survival of a subgroup of patients with certain cytogenetic abnormalities or alterations (collectively referred to as high-risk multiple myeloma) has remained poor despite aggressive therapy incorporating almost every available drug and treatment modality. Therefore, there remains a need for new and better drugs and regimens or strategies to overcome high-risk prognostic factors and improve response rates and survival rates in this patient population.

DESCRIPTION

Unless otherwise defined, all technical and scientific terms used herein have the same meaning as commonly understood by one of ordinary skill in the art to which this disclosure belongs.

Terms used herein shall be accorded the following defined meanings, unless otherwise indicated.

"Treatment" shall mean the use of a therapy to prevent or inhibit further tumor growth, as well as to cause shrinkage of a tumor or tumor burden, and to provide longer survival times. Treatment is also intended to include prevention of metastasis of tumor. A tumor is "inhibited" or "treated" if at least one symptom (as determined by responsiveness/non-responsiveness, time to progression, or indicators known in the art and described herein) of the cancer or tumor is alleviated, terminated, slowed, minimized, or prevented.

"Treatment regimen" as used herein, refers to treatment with a molecule alone, or in combination with another molecule. A treatment regimen also refers to dose amount, the frequency of dosing and the number of times a molecule, or combination of molecules, is administered.

As used herein, a "favorable" outcome or prognosis refers to long term survival, long time-to-progression (TTP), and/or good response. Conversely, an "unfavorable" outcome or prognosis refers to short term survival, short time-to-progression (TTP) and/or poor response.

As used herein, "long time-to-progression, "long TTP" and "short time-to-progression," "short TTP" refer to the amount of time until when the stable disease brought by treatment converts into an active disease. On occasion, a treatment results in stable disease which is neither a good nor a poor response, e.g., MR, the disease merely does not get worse, e.g., become a progressive disease, for a period of time. This period of time can be at least 4-8 weeks, at least 3-6 months or more than 6 months.

The term "survival" refers to the patient remaining alive, and includes progression-free survival (PFS) and overall survival (OS). Survival can be estimated by the Kaplan-Meier method, and any differences in survival are computed using the stratified log-rank test.

The term "progression-free survival (PFS)" refers to the time from treatment (or randomization) to first disease progression or death. For example it is the time that the patient remains alive, without return of the cancer (e.g., for a defined period of time such as about one month, two months, three months, three and a half months, four months, five months, six months, seven months, eight months, nine months, about one year, about two years, about three years, about five years, about 10 years, about 15 years, about 20 years, about 25 years, etc.) from initiation of treatment or from initial diagnosis. Progression free survival can be measured in multiple myeloma by using International Myeloma Working Group (IMWG) criteria.

The term "overall survival" refers to the patient remaining alive for a defined period of time (such as about one year, about two years, about three years, about four years, about five years, about 10 years, about 15 years, about 20 years, about 25 years, etc.) from initiation of treatment or from initial diagnosis.

The term "proteasome-mediated disorder" refers to any disorder, disease or condition which is caused or characterized by an increase in proteasome expression or activity, or which requires proteasome activity. The term "proteasome-mediated disorder" also includes any disorder, disease or condition in which inhibition of proteasome activity is beneficial. Proteasome inhibitors are drugs that block the action of proteasomes, cellular complexes that break down proteins, like the p53 protein. Proteasome inhibitors are being studied in the treatment of cancer, especially multiple myeloma. Examples of proteasome inhibitors are bortezomib, carfilzomib, ixazomib, disulfiram, epigallocatechin-3-gallate, salinosporamid A, ONX0912, CEP-18770, and epoxomicin.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "comprises" refers to "includes, but is not limited to."

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The term "orally" refers to administering a composition that is intended to be ingested. Examples of oral forms include, but are not limited to, tablets, pills, capsules, powders, granules, solutions or suspensions, and drops. Such forms may be swallowed whole or may be in chewable form.

The term "patient", as used herein, means an animal, preferably a mammal, more preferably a human.

A "cytogenetic alteration" is a chromosomal change such as a deletion, duplication, or translocations in a chromosome.

A "kit" is any article of manufacture (e.g., a package or container) comprising at least one reagent, e.g. a probe, for specifically detecting one or more cytogenetic alterations of the disclosure. The article of manufacture may be promoted, distributed, sold or offered for sale as a unit for performing, e.g., in vitro, the methods of the present disclosure, e.g., on a sample having been obtained from a patient. The reagents included in such a kit can comprise probes/primers and/or antibodies for use in detecting one or more cytogenetic alterations. In addition, a kit of the present disclosure can contain instructions which describe a suitable detection assay. Such a kit can be conveniently used, e.g., in a clinical or a contract testing setting, to generate information to be recorded, stored, transmitted or received to allow for diagnosis, evaluation or treatment of patients exhibiting symptoms of multiple myeloma.

As used herein, the term "evaluating a patient" refers to the act of reviewing or analyzing a patient's cytogenetic alteration. The evaluation can further include one or more of: obtaining a sample from a patient (e.g. a sample from a bodily fluid (e.g. a blood sample, a serum sample, a urine sample, a synovial fluid sample, a tear sample, a saliva sample) or a tissue sample (e.g., a skin sample or a tissue sample obtained from a biopsy) or analyzing a sample in vivo; assaying the sample or requesting an assay using the sample to obtain genomic information regarding the patient's cytogenetic alteration; reviewing the patient's information using the assay results performed with the sample and/or a patient's medical records. The patient's information (e.g. genomic information or value on the patient's cytogenetic alteration) can then optionally be compared to a reference standard, e.g., publicly available information (i.e. against a reference population), to make an informed decision regarding treatment options for that patient.

The terms "boronate ester" and "boronic ester" are used interchangeably and refer to a chemical compound containing a —B($Z^1$)($Z^2$) moiety, wherein $Z^1$ and $Z^2$ together form a cyclic boronic ester having 2-20 carbon atoms, and optionally one or more heteroatoms selected from N, S, or O.

In some embodiments, the present disclosure provides a method of treating a patient having multiple myeloma, comprising:
(i) determining if the patient has a cytogenetic alteration at chromosome 17, and
(ii) if the patient has a cytogenetic alteration at chromosome 17, then administering to a patient in need thereof a treatment regimen comprising a compound of formula (I):

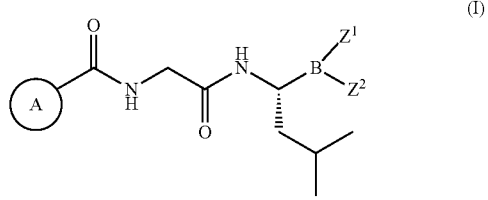

or a pharmaceutically acceptable salt, stereoisomeric or tautomeric form thereof, wherein ring A is

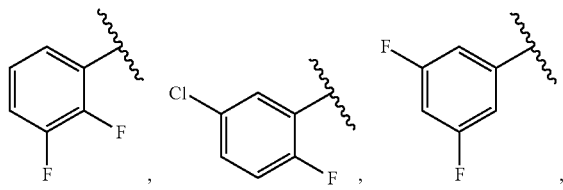

-continued

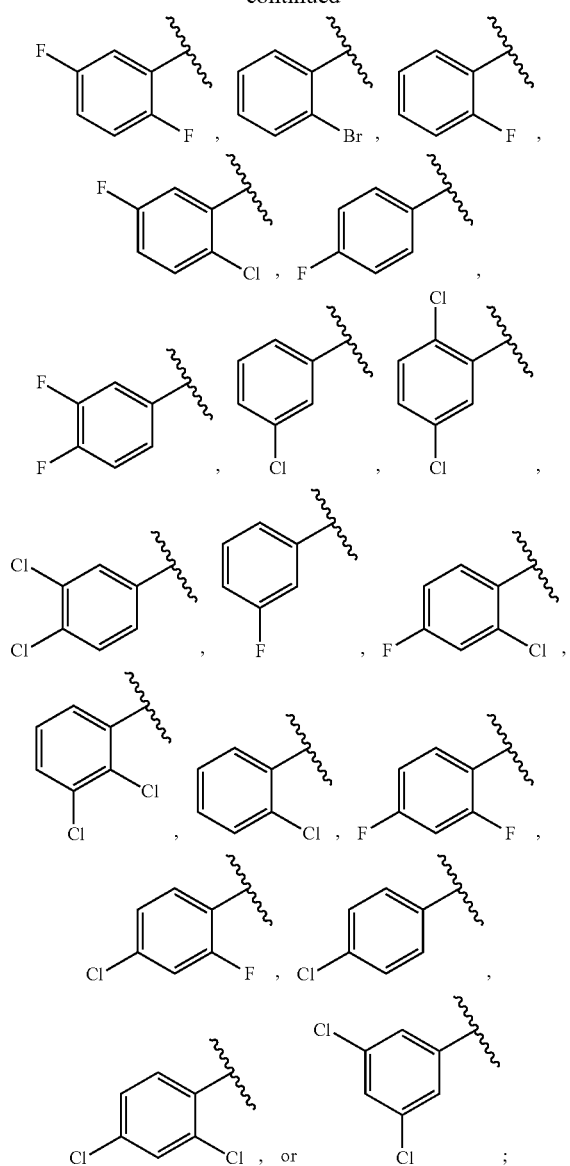

and

Z¹ and Z² are each independently hydroxyl; or Z¹ and Z² together form a cyclic boronic ester having 2-20 carbon atoms, and optionally one or more heteroatoms selected from N, S, or O.

In some embodiments, the compound of formula (I) is characterized by formula (Ia):

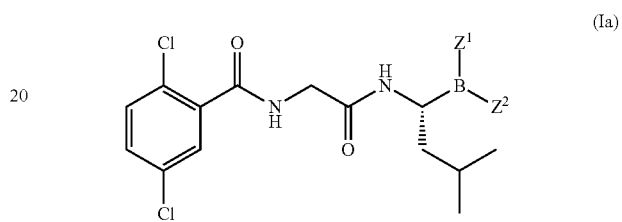

or a pharmaceutically acceptable salt, stereoisomeric or tautomeric form thereof, wherein:
$Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure provides a method of treating a patient having multiple myeloma, comprising:
(i) determining if the patient has a cytogenetic alteration at chromosome 17, and
(ii) if the patient has a cytogenetic alteration at chromosome 17, then administering to a patient in need thereof a treatment regimen comprising a compound of formula (Ia):

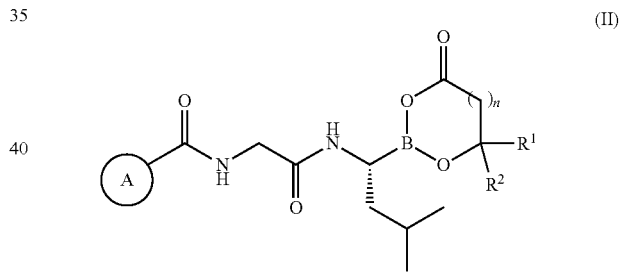

or a pharmaceutically acceptable salt, stereoisomeric or tautomeric form thereof, wherein:
$Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the compound of formula (I) is characterized by formula (II):

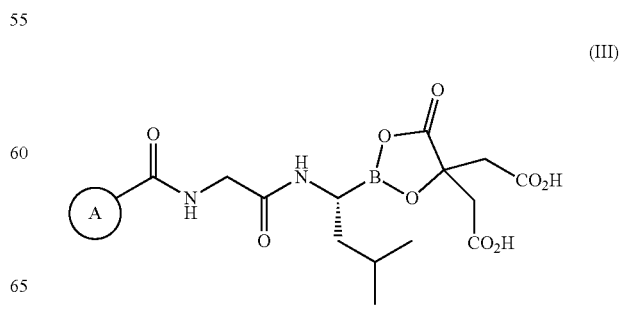

or a pharmaceutically acceptable salt, stereoisomeric or tautomeric form thereof, wherein:
ring A is defined above; $R^1$ and $R^2$ independently is $-(CH_2)_p-CO_2H$; wherein one of carboxylic acids optionally forms a further bond with the boron atom; n is 0 or 1; and p is 0 or 1.

In some embodiments, the compound of formula (I) is characterized by formula (III):

or a pharmaceutically acceptable salt, stereoisomeric or tautomeric form thereof, wherein ring A is defined above.

In some embodiments, the compound of formula (I) is characterized by formula (IIIa):

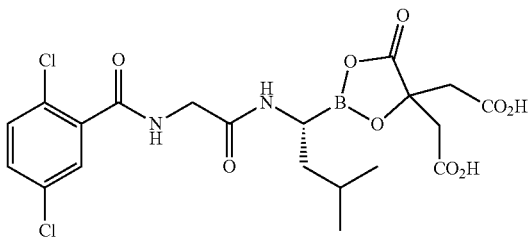

(IIIa)

or a pharmaceutically acceptable salt, stereoisomeric or tautomeric form thereof.

In some embodiments, the compound of formula (I) is characterized by formula (IV):

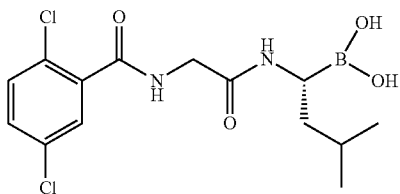

(IV)

or an ester or a pharmaceutically acceptable salt thereof.

In some embodiments, the compound of formula (I) is characterized by formula (IIIa). In some embodiments, the compound of formula (I) is characterized by formula (IV). In some embodiments, the compound of formula (Ia) is characterized by formula (IIIa). In some embodiments, the compound of formula (Ia) is characterized by formula (IV).

The compound of formula (IV), also known as ixazomib, is a peptide boronic acid developed by Millennium Pharmaceuticals, Inc. Ixazomib is a biologically active molecule that potently, reversibly, and selectively inhibits the proteasome. The compound of formula (IIIa) is a citrate ester of ixazomib, referred to as ixazomib citrate herein. Ixazomib citrate rapidly hydrolyzes to ixazomib upon contact with either plasma or aqueous solutions.

In some embodiments, the compound of formulas (I), (Ia), (II), (III), (IIIa) or (IV) are administered orally. In some embodiments, the compound of formula (I), (Ia), (II), (III), (IIIa) or (IV) is administered in a solid dosage form. In some embodiments, the solid dosage form is a capsule. In some embodiment, the capsule comprises a mixture of the compound of formula (IIIa) or a pharmaceutically acceptable salt thereof, microcrystalline cellulose, talc and magnesium stearate. In some embodiments the capsule comprises a mixture of the compound of formula (IIIa), microcrystalline cellulose, talc and magnesium stearate.

Synthetic methods for the preparation of compounds and pharmaceutical compositions of compounds of formulas (I), (Ia), (II), (III), (IIIa) and (IV) are, for example, described in U.S. Pat. Nos. 7,442,830, 7,687,662, 8,003,819, 8,530,694, and International Patent Publication WO 2009/154737, which are hereby incorporated by reference specifically and in their entirety.

In some embodiments, the compound of formula (I) is administered on each of days 1, 8 and 15 of a 28 day cycle. In some embodiments, the compound of formula (Ia) is administered on each of days 1, 8 and 15 of a 28 day cycle. In some embodiments, the compound of formula (IIIa) is administered on each of days 1, 8 and 15 of a 28 day cycle. In some embodiments, the compound of formula (IV) is administered on each of days 1, 8 and 15 of a 28 day cycle.

In some embodiments, the amount of the compound of formula (IV) that is administered is 4 mg, 3 mg or 2.3 mg. In some embodiments, the amount of the compound of formula (IV) that is administered is 4 mg. In some embodiments, the amount of the compound of formula (IV) that is administered is 3 mg. In some embodiments, the amount of the compound of formula (IV) that is administered is 2.3 mg. In some embodiments, the amount of the compound of formula (IIIa) that is contained in a capsule is 5.7 mg equivalent to 4 mg of the compound of formula (IV). In some embodiments, the amount of the compound of formula (IIIa) that is contained in a capsule is 4.3 mg equivalent to 3 mg of the compound of formula (IV). In some embodiments, the amount of the compound of formula (IIIa) that is contained in a capsule is 3.3 mg equivalent to 2.3 mg of the compound of formula (IV).

In some embodiments, the treatment regimen further comprises additional therapeutic agents. In some embodiments, the additional therapeutic agent is an immunomodulatory drug. Examples of immunomodulatory drugs include lenalidomide and pomalidomide. In some embodiments, the immunomodulatory drug is lenalidomide. In some embodiments, the amount of lenalidomide that is administered is 25 mg. In some embodiments, lenalidomide is administered on each of days 1-21 of a 28 day cycle.

In some embodiments, the additional therapeutic agent is a steroid. Examples of steroids include dexamethasone and prednisone. In some embodiments, the additional therapeutic agent is dexamethasone. In some embodiments, the amount of dexamethasone that is administered is 40 mg. In some embodiments, dexamethasone is administered on each of days 1, 8, 15 and 22 of a 28-day cycle.

In some embodiments, the additional therapeutic agents are lenalidomide and dexamethasone. In some embodiments, lenalidomide is administered on each of days 1-21 of a 28 day cycle and dexamethasone is administered on each of days 1, 8, 15 and 22 of a 28-day cycle.

In some embodiments, the patient with multiple myeloma has newly diagnosed multiple myeloma. In some embodiments, the patient with multiple myeloma has relapsed and/or refractory multiple myeloma. In some embodiments, the patient with multiple myeloma has relapsed multiple myeloma. In some embodiments, the patient with multiple myeloma has refractory myeloma.

The initiation and progression of multiple myeloma may be influenced by multiple mutations in different pathways and genes of the plasma cell. There can be multiple generic events that lead to disease progression and treatment resistant disease. Primary genetic events include IgH translocations and hyperdiploidy, while secondary genetic events include copy number abnormalities, DNA hypomethylation and acquired mutations. Biran et al., Risk Stratification in Multiple Myeloma, Part 1, Characterization of High-Risk Disease, Hematology and Oncology, 11, August 2013 (8) page 489-503.

Guidelines from the International Myeloma Working Group support a comprehensive cytogenetic evaluation in all patients at the time of diagnosis and at relapse. These recommendations include detecting cytogenetic alterations by interphase FISH (Fluorescent In Situ Hybridization) in purified plasma cells or in combination with immunofluorescent detection of light-chain-restricted plasma cells (cIg-FISH).

In multiple myeloma, cytogenetic alterations that can be detected by FISH include, but are not limited to, t(4:14), t(14:16) and del (17).

Del (17p)

The majority of chromosome 17 deletions are hemizygous or impact the whole p arm. This genetic event is observed in approximately 10% of new myeloma cases with the frequency increasing in later disease stages (Fonseca et al., Blood. 2003 Jun. 1; 101(11):4569-75; Tiedemann et al., Leukemia (2008) 22, 1044-1052). The relevant gene deregulated in del(17p) is thought to be the tumor suppressor gene, tumor protein p53 (TP53), e.g., the gene associated with GenBank Accession No. NM_000546, as gene expression profiling (GEP) has shown that myeloma samples with monoallelic 17p deletions express significantly less TP53 compared to non deleted samples (Walker et al., Blood. 2010 Oct. 14; 116(15):e56-65). Thus in some cells, the TP53 gene can be deleted as a result of del 17p deletion. In cases without del(17p) the rate of TP53 mutation is <1%, whereas in cases with del(17p) this rises to 25-37% (Lode et al., Haematologica November 2010; 95(11):1973-6); a finding providing some evidence that monoallelic 17p deletion contributes to disruption of the remaining allele. The TP53 gene has been mapped to 17p13 and is known to function as a transcriptional regulator influencing cell cycle arrest, DNA repair, and apoptosis in response to DNA damage. Del(17p) is the most important molecular finding for prognostication in multiple myeloma as it is linked to an aggressive disease phenotype, a greater degree of extramedullary disease, and shortened survival (Fonseca et al., Blood. 2003 Jun. 1; 101(11):4569-75, Avet-Loiseau et al., Blood. 2007 Apr. 15; 109(8):3489-95).

t(4:14) and t(14:16)

IGH translocations are detectable in approximately 40% of multiple myeloma (MM) patients. Most of the translocations detected in MM lead to alteration of the cell cycle control, which is a unifying event in early pathogenesis of MM (Bergsagel et al., Blood, 2005; 106(1):296-303). The t(4:14) translocation is detected in about 15% of patients. T(4:14) leads to upregulation of two genes multiple myeloma SET domain (MMSET, also known as Wolf-Hirschhorn syndrome candidate 1, WHSC1) and fibroblast growth factor receptor 3 (FGFR3), a receptor tyrosine kinase MMSET protein has histone methylation activity and among the several genes affected by its activity there are several cell cycle—related genes, such as Cyclin E2, E2F transcription factor 2 (E2F2), tumor protein p53 inducible nuclear protein 1 (Tp53INP1) and cell division cycle 25A (CDC25A).

The translocation t(14:16) is seen in about 6% of multiple myeloma patients and has also been associated with unfavorable prognosis in multiple myeloma. It contains the MAF transcription factor family, which is upregulated as a result of this translocation. (Bergsagel et al., Blood. 2005; 106(1): 296-303).

In some aspects, the present disclosure provides methods for the treatment of multiple myeloma in patients who have one or more of the cytogenetics alterations described above. In some embodiments, the cytogenetic alteration is a deletion in chromosome 17. In some embodiments, the cytogenetic alteration is del (17). As used herein, the terms del (17) and del (17p) are used interchangeably. In some embodiments, the cytogenetic alteration is del (17p13). In some embodiments, there is at least one other cytogenetic alteration. In some embodiments, the at least one other cytogenetic alteration is t(4:14). In some embodiments, the at least one other cytogenetic alteration is t(14:16). In some embodiments, there is at least two other cytogenetic alterations. In some embodiments, the at least two other cytogenetic alterations are t(4:14) and t(14:16). In some embodiments, the cytogenetic alternation is at least one of del(17), t(4:14), or t(14:16).

In some embodiments, the cytogenetic alterations are del (17) and t(4:14). In some embodiments, the cytogenetic alternations are del (17) and t(14:16). In some embodiments, the cytogenetic alterations are del (17), t(4:14) and t(14:16). In some embodiments, the cytogenetic alteration is t(4:14). In some embodiments, the cytogenetic alteration is t(14:16). In some embodiments, the cytogenetic alterations are del (17) and at least one of t(4:14) and t(14:16).

In some embodiments, the present disclosure relates to methods of treating a patient having multiple myeloma, comprising:
(i) selecting a patient based upon the patient having a cytogenetic alteration at chromosome 17; and
(ii) administering to the patient a treatment regimen comprising a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure relates to methods of evaluating a patient having multiple myeloma for responsiveness to a treatment regimen comprising a compound of formula (Ia) or a pharmaceutically acceptable salt, stereoisomeric or tautomeric form thereof, wherein: $Z^1$ and $Z^2$ are each independently hydroxyl; or $Z^1$ and $Z^2$ together form a cyclic boronic ester having 2-20 carbon atoms, and optionally one or more heteroatoms selected from N, S, or O; comprising the steps:
i) determining whether a patient has a cytogenetic alteration at chromosome 17;
ii) recording the presence or absence of a cytogenetic alteration at chromosome 17, and
iii) determining, recommending or selecting an appropriate treatment regimen based upon the presence or absence of a cytogenetic alteration at chromosome 17.

In some embodiments, step iii) comprises determining whether to begin or continue the treatment regimen comprising the compound of formula (Ia) or a pharmaceutically acceptable salt, stereoisomeric or tautomeric form thereof, based upon the presence of a cytogenetic alteration at chromosome 17.

The identification of a correlation between a cytogenetic alteration that a patient with multiple myeloma has and clinical responsiveness to a treatment regimen comprising a compound of formula (Ia), can be the basis for designing a diagnostic method to predict those individuals who will respond to a treatment regimen compromising a compound of formula (Ia). Alternatively, such methods can also be used to predict individuals who will respond to a treatment regimen comprising a compound of formula (Ia) versus a treatment regimen not comprising a compound of formula (Ia).

The methods for evaluating a patient having multiple myeloma for responsiveness or non-responsiveness to a treatment regimen comprising a compound of formula (Ia) can include an additional step of recording the value of a parameter related to the patient's cytogenetic alteration status.

"Recording" as used herein, refers to the act or process of making a record capable of being accessed or referenced at a later date. In one embodiment, the record is made in writing. In one embodiment, the record is made on paper (e.g., written in a patient's medical record or written on a batch record), or the record is made in an electronic medium (e.g., the record is entered into a computer, for example, the record is entered into an electronic version of the patient's medical record or the record is entered into a database). In another embodiment, the record is made vocally by recording one's voice. In one embodiment, the voice recording is made on, for example, a tape or compact disk. In one embodiment, the recorded information contains reference standard value(s).

The methods for evaluating a patient having multiple myeloma for responsiveness or non-responsiveness to a treatment regimen comprising a compound of formula (Ia) can include a further step of determining, recommending or selecting an appropriate treatment regimen.

As used herein, "determining an appropriate treatment regimen" refers to the act or process of reviewing a patient's genotype; and, optionally, reviewing the patient's medical history (e.g., for allergies or intolerances to certain types of drugs, or for drug incompatibilities) and assessing the likelihood that the patient will be responsive to a given treatment regimen.

In some embodiments, determining if a patient has a cytogenetic alteration refers to detecting a cytogenetic alteration, for example in a sample from the patient. In some embodiments, detecting a cytogenetic alternation can be followed by treatment as described herein.

As used herein, "recommending an appropriate treatment regimen" refers to the act or process of suggesting, for example, to the patient, to a family member or caregiver of the patient, or to medical personnel (e.g., the patient's primary care physician), a treatment regimen which is perceived as being favorable for the patient. As used herein, a recommendation can be a written or a verbal recommendation.

As used herein, "selecting an appropriate treatment regimen" refers to the act or process of picking or choosing a treatment regimen from other treatment regimen options for a patient. In one embodiment, the selection is made upon review of i) the patient's genotype; and/or ii) the patient's medical history (e.g., for allergies or intolerances to certain types of drugs, for drug incompatibilities and for treatment history) and assessing the likelihood that the patient will be responsive to a given treatment regimen. In another embodiment, the selection is made based upon a recommendation.

In some embodiments, the present disclosure provides a method of treating a patient having multiple myeloma, comprising:
(iii) determining if the patient has a cytogenetic alteration at cytogenetic alteration t(4:14); and
(iv) if the patient has a cytogenetic alteration t(4:14), then administering to a patient in need thereof a treatment regimen comprising a compound of formula (I):

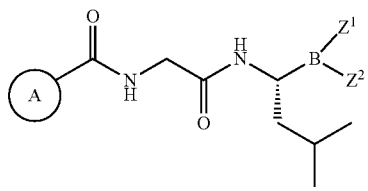

(I)

or a pharmaceutically acceptable salt, stereoisomeric or tautomeric form thereof, wherein ring A is

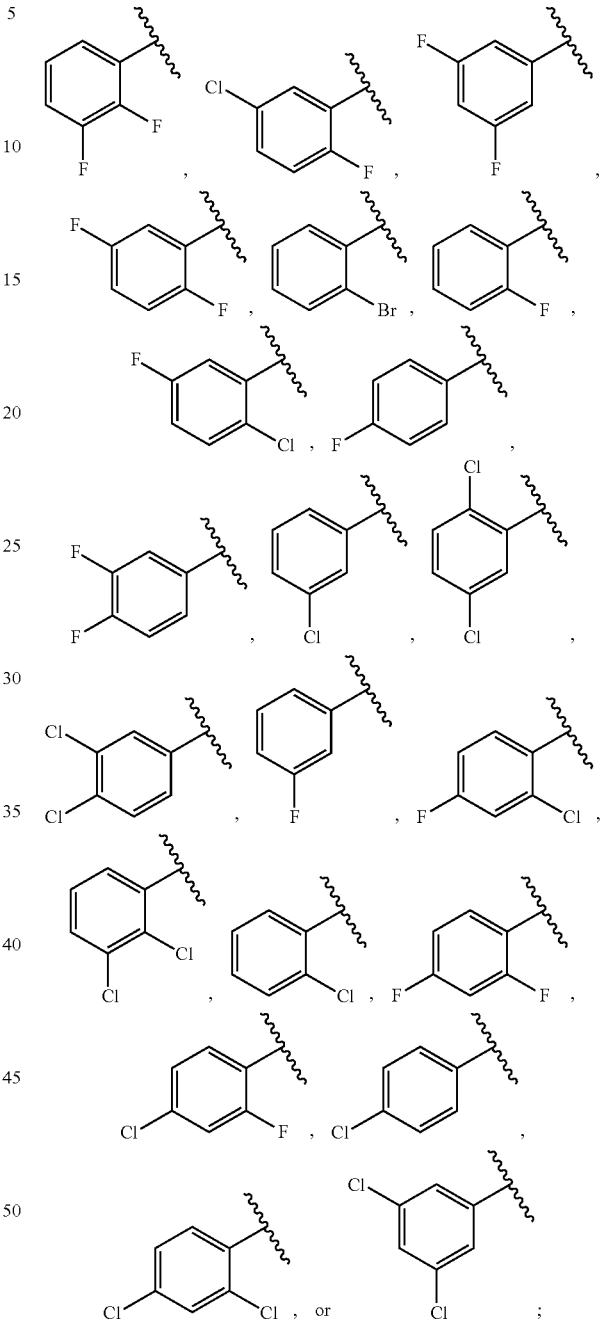

and $Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure provides a method of treating a patient having multiple myeloma, comprising:
(i) determining if the patient has a cytogenetic alteration t(4:14); and (ii) if the patient has a cytogenetic alteration at t(4:14), then administering to a patient in need thereof a treatment regimen comprising a compound of formula (Ia):

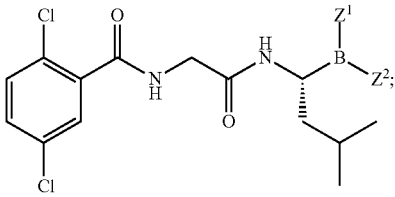

(Ia)

or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure provides a use of a compound of formula (Ia) for treating a patient having multiple myeloma, wherein the use comprises:
(i) determining if the patient has a cytogenetic alteration at chromosome 17, and
(ii) if the patient has a cytogenetic alteration at chromosome 17, selecting the patient for administration of a treatment regimen comprising a compound of formula (Ia):

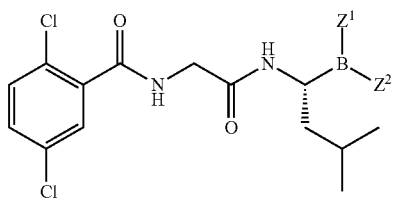

(Ia)

or a pharmaceutically acceptable salt, stereoisomeric or tautomeric form thereof, wherein:
$Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure relates to methods of treating a patient having multiple myeloma, comprising:
(i) selecting a patient based upon the patient having a cytogenetic alteration t(4:14); and
(ii) administering to the patient a treatment regimen comprising a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure relates to use of a compound of formula (Ia) for treating a patient having multiple myeloma, comprising:
i) selecting a patient, based upon the patient having a cytogenetic alteration at chromosome 17, for administration of a treatment regimen comprising a compound of formula (Ia):

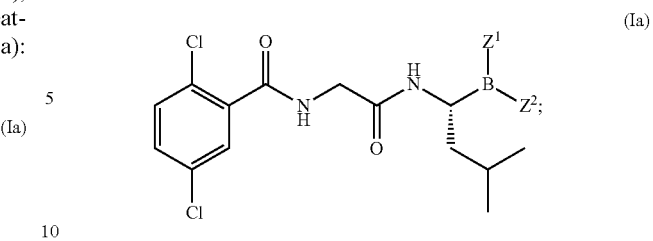

(Ia)

or a pharmaceutically acceptable salt, stereoisomeric or tautomeric form thereof, wherein:
$Z^1$ and $Z^2$ are each independently hydroxyl; or $Z^1$ and $Z^2$ together form a cyclic boronic ester having 2-20 carbon atoms, and optionally one or more heteroatoms selected from N, S, or O.

In some embodiments, the present disclosure relates to methods of evaluating a patient having multiple myeloma for responsiveness to a treatment regimen comprising a compound of formula (Ia) or a pharmaceutically acceptable salt, stereoisomeric or tautomeric form thereof, wherein: $Z^1$ and $Z^2$ are each independently hydroxyl; or $Z^1$ and $Z^2$ together form a cyclic boronic ester having 2-20 carbon atoms, and optionally one or more heteroatoms selected from N, S, or O comprising the steps:
(i) determining whether a patient has a cytogenetic alteration t(4:14);
(ii) recording the presence or absence of a cytogenetic alteration t(4:14), and
(iii) determining, recommending or selecting an appropriate treatment regimen based upon the presence or absence of a cytogenetic alteration t(4:14).

In some embodiments, step iii) comprises determining whether to begin or continue the treatment regimen comprising the compound of formula (Ia) or a pharmaceutically acceptable salt, stereoisomeric or tautomeric form thereof, based upon the presence of a cytogenetic alteration t(4:14).

In some embodiments, determining if a patient has a cytogenetic alteration comprises the steps of:
(i) providing a bone marrow aspirate sample from the patient;
(ii) isolating CD138 positive plasma cells from the sample; and
(iii) performing FISH analysis on the CD138 enriched positive plasma cells.

In some embodiments, the sample is a bone marrow aspirate sample. In some embodiments, the sample is blood. In some embodiments, the CD138 positive plasma cells are isolated from the sample using fluorescence activated cell sorting. In some embodiments, the CD138 positive plasma cells are isolated from the sample using magnetic activated cell sorting (MACS). The magnetic or immunomagnetic beads are available from a number of commercial sources including Miltenyi Biotec (CA, USA) or Stem Cell Technologies (Vancouver, Canada)

A general principle of prognostic assays involves preparing a sample or reaction mixture that may contain a marker or a cytogenetic alteration, and a probe, under appropriate conditions and for a time sufficient to allow the marker and probe to interact and bind, thus forming a complex that can be removed and/or detected in the reaction mixture. These assays can be conducted in a variety of ways. For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay. One example of such an embodiment includes use of an array or chip which contains a predictive marker or marker set anchored for expression analysis of the sample There are many established methods for anchoring assay components to a solid phase. These include, marker, chromosome or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker, chromosome or probe belongs. Examples of supports or carriers include, but are not limited to, glass, polystyrene, nylon, polypropylene, nylon, polyethylene, dextran, amylases, natural and modified celluloses, polyacrylamides, gabbros, and magnetite. One skilled in the art may know many other suitable carriers for binding antibody or antigen, and will be able to adapt such support for use with the present disclosure. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of marker/probe complexes anchored to the solid phase can be accomplished in a number of methods outlined herein.

In an embodiment, the probe, when it is the unanchored assay component, can be labeled for the purpose of detection and readout of the assay, either directly or indirectly, with detectable labels discussed herein and which are well-known to one skilled in the art. The term "labeled", with regard to the probe (e.g., nucleic acid or antibody), is intended to encompass direct labeling of the probe by coupling (i.e., physically linking) a detectable substance to the probe, as well as indirect labeling of the probe by reactivity with another reagent that is directly labeled. An example of indirect labeling includes detection of a primary antibody using a fluorescently labeled secondary antibody. It is also possible to directly detect marker/probe complex formation without further manipulation or labeling of either component (marker or probe), for example by utilizing the technique of fluorescence energy transfer (FET, see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

As used herein, the term "hybridizes" is intended to describe conditions for hybridization and washing under which nucleotide sequences that are significantly identical or homologous to each other remain hybridized to each other. In some embodiments, the conditions are such that sequences at least about 70%, at least about 80%, at least about 85%, 90% or 95% identical to each other remain hybridized to each other for subsequent amplification and/or detection. Stringent conditions vary according to the length of the involved nucleotide sequence but are known to those skilled in the art and can be found or determined based on teachings in *Current Protocols in Molecular Biology*, Ausubel et al., eds., John Wiley & Sons, Inc. (1995), sections 2, 4 and 6. Additional stringent conditions and formulas for determining such conditions can be found in *Molecular Cloning: A Laboratory Manual*, Sambrook et al., Cold Spring Harbor Press, Cold Spring Harbor, N.Y. (1989), chapters 7, 9 and 11. A non-limiting example of stringent hybridization conditions for hybrids that are at least 10 basepairs in length includes hybridization in 4× sodium chloride/sodium citrate (SSC), at about 65-70° C. (or hybridization in 4×SSC plus 50% formamide at about 42-50° C.) followed by one or more washes in 1×SSC, at about 65-70° C. A non-limiting example of highly stringent hybridization conditions for such hybrids includes hybridization in 1×SSC, at about 65-70° C. (or hybridization in 1×SSC plus 50% formamide at about 42-50° C.) followed by one or more washes in 0.3×SSC, at about 65-70° C. A non-limiting example of reduced stringency hybridization conditions for such hybrids includes hybridization in 4×SSC, at about 50-60° C. (or alternatively hybridization in 6×SSC plus 50% formamide at about 40-45° C.) followed by one or more washes in 2×SSC, at about 50-60° C. Ranges intermediate to the above-recited values, e.g., at 65-70° C. or at 42-50° C. are also intended to be encompassed by the present disclosure. Another example of stringent hybridization conditions are hybridization in 6× sodium chloride/sodium citrate (SSC) at about 45° C., followed by one or more washes in 0.2×SSC, 0.1% SDS at 50-65° C. A further example of stringent hybridization buffer is hybridization in 1 M NaCl, 50 mM 2-(N-morpholino) ethanesulfonic acid (MES) buffer (pH 6.5), 0.5% sodium sarcosine and 30% formamide. SSPE (1×SSPE is 0.15M NaCl, 10 mM $NaH_2PO_4$, and 1.25 mM EDTA, pH 7.4) can be substituted for SSC (1×SSC is 0.15M NaCl and 15 mM sodium citrate) in the hybridization and wash buffers; washes are performed for 15 minutes each after hybridization is complete The hybridization temperature for hybrids anticipated to be less than 50 base pairs in length should be 5-10° C. less than the melting temperature ($T_m$) of the hybrid, where $T_m$ is determined according to the following equations. For hybrids less than 18 base pairs in length, $T_m(°C.)=2(\#\text{of A+T bases})+4(\#\text{of G+C bases})$. For hybrids between 18 and 49 base pairs in length, $T_m(°C.)=81.5+16.6(\log_{10}[\text{Na}^+])+0.41(\%\text{ G+C})-(600/N)$, where N is the number of bases in the hybrid, and [Na$^+$] is the concentration of sodium ions in the hybridization buffer ([Na$^+$] for 1×SSC=0.165 M). It will also be recognized by the skilled practitioner that additional reagents may be added to hybridization and/or wash buffers to decrease non-specific hybridization of nucleic acid molecules to membranes, for example, nitrocellulose or nylon membranes, including but not limited to blocking agents (e.g., BSA or salmon or herring sperm carrier DNA), detergents (e.g., SDS), chelating agents (e.g., EDTA), Ficoll, polyvinylpyrrolidone (PVP) and the like. When using nylon membranes, in particular, an additional non-limiting example of stringent hybridization conditions is hybridization in 0.25-0.5M NaH$_2$PO$_4$, 7% SDS at about 65° C., followed by one or more washes at 0.02M NaH$_2$PO$_4$, 1% SDS at 65° C., see e.g., Church and Gilbert (1984) *Proc. Natl. Acad. Sci. USA* 81:1991-1995, (or alternatively 0.2×SSC, 1% SDS). A primer or nucleic acid probe can be used alone in a detection method, or a primer can be used together with at least one other primer or nucleic acid probe in a detection method. Primers can also be used to amplify at least a portion of a nucleic acid. Nucleic acid probes of the disclosure refer to nucleic acids which hybridize to the region of interest and which are not further extended. For example, a nucleic acid probe is a nucleic acid which specifically hybridizes to a mutant region of a biomarker, and which by hybridization or absence of hybridization to the DNA of a patient or the type of hybrid formed can be indicative of the presence or identity of the mutation of the biomarker or the amount of marker activity.

In one format, the RNA is immobilized on a solid surface and contacted with a probe, for example by running the isolated RNA on an agarose gel and transferring the RNA from the gel to a membrane, such as nitrocellulose. In an alternative format, the nucleic acid probe(s) are immobilized on a solid surface and the RNA is contacted with the probe(s), for example, in an AFFYMETRIX® gene chip array or a SNP chip (Santa Clara, Calif.) or customized array using a marker set comprising at least one marker indicative of treatment outcome. A skilled artisan can readily adapt known RNA and DNA detection methods for use in detecting the amount of the markers of the present disclosure. For example, the high density microarray or branched DNA assay can benefit from a higher concentration of tumor cell in the sample, such as a sample which had been modified to isolate tumor cells as described in earlier sections. In a related embodiment, a mixture of transcribed polynucleotides obtained from the sample is contacted with a substrate having fixed thereto a polynucleotide complementary to or homologous with at least a portion (e.g., at least 7, 10, 15, 20, 25, 30, 40, 50, 100, 500, or more nucleotide residues or 10 to 50, 15 to 40 or 15 to 30 consecutive nucleotides) of a marker nucleic acid. If polynucleotides complementary to or homologous with the marker are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). In an embodiment when a method of assessing marker expression is used which involves hybridization of one nucleic acid with another, the hybridization can be performed under stringent hybridization conditions.

In an embodiment, a mutation in a marker can be identified by sequencing a nucleic acid, e.g., a DNA, RNA, cDNA, genomic DNA or a protein correlated with the marker gene. There are several sequencing methods known in the art to sequence nucleic acids. A primer can be designed to bind to a region comprising a potential mutation site or can be designed to complement the mutated sequence rather than the wild type sequence. Primer pairs can be designed to bracket a region comprising a potential mutation in a marker gene. A primer or primer pair can be used for sequencing one or both strands of DNA corresponding to the marker gene. A primer can be used in conjunction with a probe to amplify a region of interest prior to sequencing to boost sequence amounts for detection of a mutation in a marker gene. Examples of regions which can be sequenced include an entire gene, transcripts of the gene and a fragment of the gene or the transcript, e.g., one or more of exons or untranslated regions. Examples of mutations to target for primer selection and sequence or composition analysis can be found in public databases which collect mutation information, such as COSMIC and dbGaP.

In an embodiment, DNA, e.g., genomic DNA corresponding to the wild type or mutated marker can be analyzed both by in situ and by in vitro formats in a biological sample using methods known in the art. DNA can be directly isolated from the sample or isolated after isolating another cellular component, e.g., RNA or protein. Kits are available for DNA isolation, e.g., QIAAMP® DNA Micro Kit (Qiagen, Valencia, Calif.). DNA also can be amplified using such kits.

In one embodiment, expression of a marker is assessed by preparing mRNA/cDNA (i.e., a transcribed polynucleotide) from cells in a patient sample, and by hybridizing the mRNA/cDNA with a reference polynucleotide which is a complement of a marker nucleic acid, or a fragment thereof. cDNA can, optionally, be amplified using any of a variety of polymerase chain reaction methods prior to hybridization with the reference polynucleotide. Expression of one or more markers likewise can be detected using quantitative PCR to assess the level of expression of the marker(s). An example of the use of measuring mRNA levels is that an inactivating mutation in a marker gene can result in an altered level of mRNA in a cell. The level can be upregulated due to feedback signaling protein production in view of nonfunctional or absent protein or downregulated due to instability of an altered mRNA sequence. Alternatively, any of the many known methods of detecting mutations or variants (e.g. single nucleotide polymorphisms, deletions, etc., discussed above) of a marker of the disclosure may be used to detect occurrence of a mutation in a marker gene in a patient.

An example of direct measurement is quantification of transcripts. As used herein, the level or amount of expression refers to the absolute amount of expression of an mRNA encoded by the marker or the absolute amount of expression of the protein encoded by the marker. As an alternative to making determinations based on the absolute expression amount of selected markers, determinations may be based on normalized expression amounts. Expression amount can be normalized by correcting the absolute expression level of a marker upon comparing its expression to the expression of a control marker that is not a marker, e.g., in a housekeeping role that is constitutively expressed. Suitable markers for normalization also include housekeeping genes, such as the actin gene or beta-2 microglobulin. Reference markers for data normalization purposes include markers which are ubiquitously expressed and/or whose expression is not regulated by oncogenes. Constitutively expressed genes are known in the art and can be identified and selected according to the relevant tissue and/or situation of the patient and the analysis methods. Such normalization allows one to compare the expression level in one sample, to another sample, e.g., between samples from different times or different subjects. Further, the expression level can be provided as a relative expression level. The baseline of a genomic DNA sample, e.g., diploid copy number, can be determined by measuring amounts in cells from subjects without a tumor or in non-tumor cells from the patient. To determine a relative amount of a marker or marker set, the amount of the marker or marker set is determined for at least 1, or 2, 3, 4, 5, or more samples, e.g., 7, 10, 15, 20 or 50 or more samples in order to establish a baseline, prior to the determination of the expression level for the sample in question. To establish a baseline measurement, the mean amount or level of each of the markers or marker sets assayed in the larger number of samples is determined and this is used as a baseline expression level for the biomarkers or biomarker sets in question. The amount of the marker or marker set determined for the test sample (e.g., absolute level of expression) is then divided by the baseline value obtained for that marker or marker set. This provides a relative amount and aids in identifying abnormal levels of marker protein activity.

Probes based on the sequence of a nucleic acid molecule of the disclosure can be used to detect transcripts or genomic sequences corresponding to one or more markers of the disclosure. The probe can comprise a label group attached thereto, e.g., a radioisotope, a fluorescent compound, an enzyme, or an enzyme co-factor. Such probes can be used as part of a diagnostic test kit for identifying cells or tissues which express the protein, such as by measuring levels of a nucleic acid molecule encoding the protein in a sample of cells from a subject, e.g., detecting mRNA levels or determining whether a gene encoding the protein has been mutated or deleted.

Primers or nucleic acid probes comprise a nucleotide sequence complementary to a specific a marker or a mutated region thereof and are of sufficient length to selectively hybridize with a marker gene or nucleic acid associated with a marker gene. Primers and probes can be used to aid in the isolation and sequencing of marker nucleic acids. In one embodiment, the primer or nucleic acid probe, e.g., a substantially purified oligonucleotide, comprises a region having a nucleotide sequence which hybridizes under stringent conditions to about 6, 8, 10, 12, or 15, 20, 25, 30, 40, 50, 60, 75, 100 or more consecutive nucleotides of a marker gene or a chromosome suspected of having a cytogenetic alteration. For example, a primer or nucleic acid probe comprises a nucleotide sequence of at least about 15 consecutive nucleotides, at least about 25 nucleotides or having from about 15 to about 20 consecutive nucleotides, 10 to 50 consecutive nucleotides, 12 to 35 consecutive nucleotides, 15 to 50 consecutive nucleotides, 20 to 100 consecutive nucleotides, 50 to 500 consecutive nucleotides, or 100 to 1000 consecutive nucleotides of the marker gene or chromosome. In some embodiments, a primer or nucleic acid probe comprising a nucleotide sequence of at least about 15 consecutive nucleotides of a chromosome to detect a cytogenetic alteration consists of no more than 200, 500, 750, 1000, 1500 or 2000 consecutive nucleotides of the chromosome. Nucleic acid analogs can be used as binding sites for hybridization. An example of a suitable nucleic acid analogue is peptide nucleic acid (see, e.g., Egholm et al., Nature 363:566 568 (1993); U.S. Pat. No. 5,539,083).

Primers or nucleic acid probes can be selected using an algorithm that takes into account binding energies, base composition, sequence complexity, cross-hybridization binding energies, and secondary structure (see Friend et al., International Patent Publication WO 01/05935, published Jan. 25, 2001; Hughes et al., Nat. Biotech. 19:342-7 (2001). Useful primers or nucleic acid probes of the disclosure bind sequences which are unique for each transcript, e.g., target mutated regions and can be used in PCR for amplifying, detecting and sequencing only that particular nucleic acid, e.g., transcript or mutated transcript. One of skill in the art can design primers and nucleic acid probes for the markers disclosed herein or related markers with similar characteristics, e.g., markers on the chromosome loci, or mutations in different regions of the same marker gene described herein, using the skill in the art, e.g., adjusting the potential for primer or nucleic acid probe binding to standard sequences, mutants or allelic variants by manipulating degeneracy or GC content in the primer or nucleic acid probe. Computer programs that are well known in the art are useful in the design of primers with the required specificity and optimal amplification properties, such as Oligo version 5.0 (National Biosciences, Plymouth, Minn.). While perfectly complementary nucleic acid probes and primers can be used for detecting the markers described herein and mutants, polymorphisms or alleles thereof, departures from complete complementarity are contemplated where such departures do not prevent the molecule from specifically hybridizing to the target region. For example, an oligonucleotide primer may have a non-complementary fragment at its 5' end, with the remainder of the primer being complementary to the target region. Alternatively, non-complementary nucleotides may be interspersed into the nucleic acid probe or primer as long as the resulting probe or primer is still capable of specifically hybridizing to the target region.

FISH (fluorescent in situ hybridization) is a cytogenetic technique developed by biomedical researchers in the early 1980s that is used to detect and localize the presence or absence of specific DNA sequences on chromosomes. See Speicher and Carter, Nat. Rev. Genet. 2005 October; 6(10) 782-792. FISH uses fluorescent probes that bind to only those parts of the chromosome with which they show a high degree of sequence complementarity. The IMWG recommends FISH testing for multiple myeloma patients on nuclei from purified plasma cells; Shi et al., Acta Medica International, July-December 2015 2(2), page 168-174.

Probes for the cytogenetic alternations del (17), t(4:14) and t(14:16) are available from a variety of commercial sources, including, for example, Empire Genomics, (Buffalo, N.Y.), Kreatech Inc., (part of Leica Biosystems, Illinois, USA) and Biocare Medical (CA, USA). Fluorescence microscopy can be used to find out where the fluorescent probe is bound to the chromosomes. Cells are fixed, then permeabilized to allow target accessibility. A target-specific probe, e.g., a probe composed of 20 oligonucleotide pairs, hybridizes to the target RNA(s) or DNA. Separate but compatible signal amplification systems enable the multiplex assay (more than two targets per assay, such as four, six, eight or more targets). Signal amplification is achieved via a series of sequential hybridization steps. At the end of the assay the samples are visualized under a fluorescence microscope or instrument that is capable of exciting the dye and detecting the emission from the dye, optionally recording images.

Preparation and hybridization process: First, a probe is constructed. The probe must be large enough to hybridize specifically with its target but not so large as to impede the hybridization process. The probe is tagged directly with fluorophores, with targets for antibodies or with biotin.

Tagging can be done in various ways, such as nick translation, or PCR using tagged nucleotides.

Secondly, an interphase or metaphase chromosome preparation is produced. The chromosomes are firmly attached to a substrate, usually glass. Repetitive DNA sequences must be blocked by adding short fragments of DNA to the sample. The probe is then applied to the chromosome DNA and incubated for approximately 12 hours while hybridizing. Several wash steps remove all unhybridized or partially hybridized probes. For microscopic detection, the results are then visualized and quantified using a microscope that is capable of exciting the dye and recording images.

If the fluorescent signal is weak, amplification of the signal may be necessary in order to exceed the detection threshold of the microscope. Fluorescent signal strength depends on many factors such as probe labeling efficiency, the type of probe, and the type of dye. Fluorescently tagged antibodies or streptavidin are bound to the dye molecule. These secondary components are selected so that they have a strong signal One way to amplify the fluorescent signal is using tyramide-based signal amplification technology which employs horseradish peroxidase (HRP) to generate high-density fluorescence labeling at the site of probe hybridization.

Based upon determining a noise level for the commercially available probe for del (17) a cut-off value of 5 cells per hundred (5%) was used to classify an individual as having del (17). In some embodiments, a cut-off value of 5% classifies an individual as having del (17). In some embodiments a cut-off value of 20% classifies an individual as having del (17). In some embodiments, a cut-off value of 60% classifies an individual as having del (17).

Pharmaceutical Compositions

The compounds and pharmaceutical compositions disclosed herein may be administered by any route, including intradermally, subcutaneously, orally, intraarterially or intravenously. In one embodiment, administration will be by the intravenous route. Parenteral administration can be provided in a bolus or by infusion.

The concentration of a disclosed compound in a pharmaceutically acceptable mixture will vary depending on several factors, including the dosage of the compound to be administered, the pharmacokinetic characteristics of the compound(s) employed, and the route of administration. The agent may be administered in a single dose or in repeat doses. Treatments may be administered daily or more frequently depending upon a number of factors, including the overall health of a patient, and the formulation and route of administration of the selected compound(s).

If a pharmaceutically acceptable salt of a compound of the present disclosure is utilized in these compositions, the salt preferably is derived from an inorganic or organic acid or base. For reviews of suitable salts, see, e.g., Berge et al, *J. Pharm. Sci.* 66:1-19 (1977) and *Remington: The Science and Practice of Pharmacy*, 20th Ed., ed. A. Gennaro, Lippincott Williams & Wilkins, 2000.

Nonlimiting examples of suitable acid addition salts include the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Suitable base addition salts include, ammonium salts, alkali metal salts, such as sodium and potassium salts, alkaline earth metal salts, such as calcium and magnesium salts, salts with organic bases, such as dicyclohexylamine, N-methyl-D-glucamine, t-butylamine, ethylene diamine, ethanolamine, and choline, and salts with amino acids such as arginine, lysine, and so forth.

Also, basic nitrogen-containing groups may be quaternized with such agents as lower alkyl halides, such as methyl, ethyl, propyl, and butyl chlorides, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The term "pharmaceutically acceptable carrier" is used herein to refer to a material that is compatible with a recipient subject, preferably a mammal, more preferably a human, and is suitable for delivering an active agent to the target site without terminating the activity of the agent. The toxicity or adverse effects, if any, associated with the carrier preferably are commensurate with a reasonable risk/benefit ratio for the intended use of the active agent.

The terms "carrier", "adjuvant", or "vehicle" are used interchangeably herein, and include any and all solvents, diluents, and other liquid vehicles, dispersion or suspension aids, surface active agents, isotonic agents, thickening or emulsifying agents, preservatives, solid binders, lubricants and the like, as suited to the particular dosage form desired. *Remington: The Science and Practice of Pharmacy*, 20th Ed., ed. A. Gennaro, Lippincott Williams & Wilkins, 2000 discloses various carriers used in formulating pharmaceutically acceptable compositions and known techniques for the preparation thereof. Except insofar as any conventional carrier medium is incompatible with the compounds of the disclosure, such as by producing any undesirable biological effect or otherwise interacting in a deleterious manner with any other component(s) of the pharmaceutically acceptable composition, its use is contemplated to be within the scope of this disclosure. Some examples of materials which can serve as pharmaceutically acceptable carriers include, but are not limited to, ion exchangers, alumina, aluminum stearate, lecithin, serum proteins, such as human serum albumin, buffer substances such as disodium hydrogen phosphate, potassium hydrogen phosphate, sodium carbonate, sodium bicarbonate, potassium carbonate, potassium bicarbonate, magnesium hydroxide and aluminum hydroxide, glycine, sorbic acid, or potassium sorbate, partial glyceride mixtures of saturated vegetable fatty acids, water, pyrogen-free water, salts or electrolytes such as protamine sulfate, disodium hydrogen phosphate, potassium hydrogen phosphate, sodium chloride, and zinc salts, colloidal silica, magnesium trisilicate, polyvinyl pyrrolidone, polyacrylates, waxes, polyethylene-polyoxypropylene-block polymers, wool fat, sugars such as lactose, glucose, sucrose, starches such as corn starch and potato starch, cellulose and its derivatives such as sodium carboxymethyl cellulose, ethyl cellulose and cellulose acetate, powdered tragacanth; malt, gelatin, talc, excipients such as cocoa butter and suppository waxes, oils such as peanut oil, cottonseed oil, safflower oil, sesame oil, olive oil, corn oil and soybean oil, glycols such as propylene glycol and polyethylene glycol, esters such as ethyl oleate and ethyl laurate, agar, alginic acid, isotonic saline, Ringer's solution, alcohols such as ethanol, isopropyl alcohol, hexadecyl alcohol, and glycerol, cyclodextrins, lubricants such as sodium lauryl sulfate and magnesium stearate, petroleum hydrocarbons such as mineral oil and petrolatum. Coloring agents, releasing agents, coating agents, sweetening, flavoring and perfuming agents, preservatives and antioxidants can also be present in the composition, according to the judgment of the formulator.

The pharmaceutical compositions of the disclosure can be manufactured by methods known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain solvents, diluents, and other liquid vehicles, dispersion or suspension aids, surface active agents, pH modifiers, isotonic agents, thickening or emulsifying agents, stabilizers and preservatives, solid binders, lubricants and the like, as suited to the particular dosage form desired.

According to another embodiment, the compositions of this disclosure are formulated for pharmaceutical administration to a mammal, preferably a human being. Such pharmaceutical compositions of the present disclosure may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, infrasternal, intrathecal, intrahepatic, intralesional and intracranial injection or infusion techniques. Preferably, the compositions are administered orally, intravenously, or subcutaneously. The formulations of the disclosure may be designed to be short-acting, fast-releasing, or long-acting. Still further, compounds can be administered in a local rather than systemic means, such as administration (e.g., by injection) at a tumor site.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, cyclodextrins, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Compositions formulated for parenteral administration may be injected by bolus injection or by timed push, or may be administered by continuous infusion.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents such as phosphates or carbonates.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this disclosure include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Compositions for use in the method of the disclosure may be formulated in unit dosage form for ease of administration and uniformity of dosage. The expression "unit dosage form" as used herein refers to a physically discrete unit of agent appropriate for the patient to be treated. It will be understood, however, that the total daily usage of the compounds and compositions of the present disclosure will be decided by the attending physician within the scope of sound medical judgment. A unit dosage form for parenteral administration may be in ampoules or in multi-dose containers.

Articles of Manufacture

In some embodiments, the present disclosure relates to an article of manufacture comprising:
i) a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O; and
ii) instructions for determining the appropriateness of use of said composition by determining whether a patient has a cytogenetic alteration at chromosome 17.

In some embodiments, the present disclosure relates to an article of manufacture comprising:
i) reagents for making a determination whether a patient has a cytogenetic alteration at chromosome 17, and
ii) instructions for determining the appropriateness of use of a pharmaceutical composition comprising a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O on the basis of said determination.

In some embodiments, the present disclosure relates to an article of manufacture comprising:
i) a pharmaceutical composition comprising a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O;
ii) reagents for making a determination whether a patient has a cytogenetic alteration at chromosome 17; and
iii) instructions for determining the appropriateness of use of a pharmaceutical composition comprising a compound of formula (Ia) or a pharmaceutically acceptable salt, stereoisomeric or tautomeric form on the basis of said determination.

In some embodiments, the present disclosure relates to the use of a reagent to determine whether a patient has a cytogenetic alteration at chromosome 17, in the manufacture of a kit for determining the appropriateness of use of a pharmaceutical composition comprising a compound of formula (Ia) or a pharmaceutically acceptable salt, stereoisomeric or tautomeric form thereof, wherein $Z^1$ and $Z^2$ are each independently hydroxyl; or $Z^1$ and $Z^2$ together form a cyclic boronic ester having 2-20 carbon atoms, and optionally one or more heteroatoms selected from N, S, or O on the basis of said determination; comprising identifying whether the patient has the cytogenetic alteration and determining to treat the patient with the compound if the patient has the cytogenetic alteration.

EXAMPLES

C16010 Clinical Trial

The study is an international, randomized, double-blind, placebo controlled clinical trial designed to compare the efficacy and safety of two treatment regimens administered until disease progression or unacceptable toxicity; ixazomib plus lenalidomide and dexamethasone versus placebo plus lenalidomide and dexamethasone in adult patients with relapsed and/or refractory multiple myeloma.

Subjects included in the study have a confirmed diagnosis of multiple myeloma, have received one to three prior therapies and met other eligibility criteria. Patients who are refractory to prior lenalidomide or proteasome inhibitor-based therapy are excluded. The primary endpoint is progression free survival (PFS) as assessed by an independent review committee blinded to treatment, per IMWG criteria.

Table 1 below provide information on the conditions and interventions for each patient group.

TABLE 1

| Arms | Assigned Interventions |
|---|---|
| Active Comparator: ixazomib + lenalidomide + dexamethasone | Drug: ixazomib + lenalidomide + dexamethasone Patients will receive single oral dose of ixazomib (4.0 mg) on days 1, 8, 15 and single oral dose of Lenalidomide (25 mg) on days 1-21 and single oral dose of Dexamethasone (40 mg) on days 1, 8, 15 and 22 every 28 days until disease progression |
| Placebo Comparator: placebo + lenalidomide + dexamethasone | Drug: Placebo + Lenalidomide + Dexamethasone Patients will receive single oral dose of Placebo on days 1, 8, 15 and single oral dose of Lenalidomide (25 mg) on days 1-21 and single oral dose of Dexamethasone (40 mg) on days 1, 8, 15 and 22 every 28 days until disease progression |

Sample Processing:

Bone marrow samples are received, CD138 positive plasma cells are isolated using magnetic bead sorting techniques. 10,000 CD138 positive enriched plasma cells are then used for cytogenetic testing using specific FISH probes to identify any cytogenetic alterations. The FISH probes are available from commercial sources and are stored and used according to the manufacturer's instructions (either dual color/dual fusion or dual or tricolor probes):

(i) ATM-p53 DNA probe (ASRs) [del (17); Kreatech, Inc. (Catalog Number 11Q001I495; 17P001I550)
(ii) 4; 14 DNA probe (ASRs) [t(4:14)] Kreatech, Inc. (Catalog Number 04P001I495, 14Q001I550)
(iii) 14; 16 DNA probe (ASRs)[t(14:16)] Kreatech, Inc. (Catalog Number 16Q001I49, 14Q001I550)

For each probe typically a total of 100 nuclei are counted by 2 technologists using fluorescent microscopes. If their scores disagree a third technologist counts additional nuclei. The following cut-offs are used to score a slide as abnormal (positive for the cytogenetic alteration):

(i) ATM/p53 del (17)>5
(ii) 4; 14 DNA probe [t(4:14)]>3
(iii) 14; 16 DNA probe [t(14:16)]>3

Results (Study C16010)

At the first interim analysis 722 patients had been randomized; 360 in the ixazomib arm and 362 in the placebo comparator arm. Cytogenetic analysis results were available for 76% of patients. Based primarily on central lab evaluation (97%), 19% of patients were determined to have high-risk cytogenetics by FISH [del (17), t(4:14) or t(14:16) including 10% del (17)]. Of the patients with high-risk cytogenetics 75 were in the ixazomib group and 62 were in the placebo group. 36 and 33 patients in the ixazomib and placebo groups, respectively, had del(17p) alone or in combination with either or both t(4:14) and t(14:16), 36 and 25 patients, respectively, had t(4:14) alone, and 3 and 4 patients, respectively, had t(14:16) alone.

Analysis of patients defined by at least del (17) showed an improvement in median PFS for patients on the ixazomib arm versus the placebo arm (21.4 months vs 9.7 months, HR=0.596). Analysis of patients defined by any of the three high-risk cytogenetic alterations (del (17), t(4:14) and t(14:16) showed an improvement in PFS for the ixazomib arm versus placebo arm (21.4 months vs 9.7 months, HR=0.543). Additional data for response rates are shown below in Table 2

As described above a cut-off value of 5 cells per hundred (5%) was used to classify a patient with a del (17). Further analysis of the data using cut-offs of 20% and 60% is shown in Table 3 below.

TABLE 3

| Cut-off for del(17p) | Number of patients | Median PFS, mos IRd vs placebo-Rd | HR | p-value |
|---|---|---|---|---|
| 5% | 69 | 21.4 vs 9.7 | 0.596 | 0.162 |
| 20% | 59 | 21.4 vs 6.7 | 0.611 | 0.2049 |
| 60% | 33 | 15.7 vs 5.1 | 0.49 | 0.2481 |

As described above a cut-off value of 3 cells per hundred (3%) was used to classify a patient with t(4:14) alone. Further analysis of the data using cut-offs of 10% and 20% is shown in Table 4 below.

TABLE 4

| Cut-off for t(4:14) alone | Number of patients | Median PFS, mos IRd vs placebo-Rd | HR | p-value |
|---|---|---|---|---|
| 3% | 61 | 18.5 vs 12 | 0.645 | 0.353 |
| 10% | 59 | 18.5 vs 12 | 0.690 | 0.444 |
| 20% | 58 | 18.5 vs 12 | 0.685 | 0.436 |

We claim:

1. A method of treating a patient having multiple myeloma, comprising:
(i) determining that the patient has a cytogenetic alteration at chromosome 17, wherein the cytogenetic alteration at chromosome 17 is del (17), and
(ii) administering to the patient a treatment regimen comprising administering about 5.7 mg, about 4 mg or about 3 mg of a compound of formula (IIIa):

TABLE 2

| | ORR, % | | ≥VGPR, % | | ≥CR, % | | Median PFS, months | | |
|---|---|---|---|---|---|---|---|---|---|
| | IRd | Placebo-Rd | IRd | Placebo-Rd | IRd | Placebo-Rd | IRd | Placebo-Rd | HR |
| All high-risk patients | 79* | 60 | 45* | 21 | 12* | 2 | 21.4 | 9.7 | 0.543[a] |
| Patients with del (17p)[†] | 72 | 48 | 39 | 15 | 11* | 0 | 21.4 | 9.7 | 0.596[b] |
| Patients with t(4; 14) alone | 89 | 76 | 53 | 28 | 14 | 4 | 18.5 | 12.0 | 0.645[c] |

*p < 0.05 for comparison between regimens.
[†]Alone or in combination with t(4; 14 or t(14; 16);
ORR = overall response rate,
VGPR = very good partial response,
CR = complete response.
[a]95% confidence interval, 0.321, 0.918;
[b]95% confidence interval, 0.29, 1.24;
[c]95% confidence interval, 0.25, 1.66.

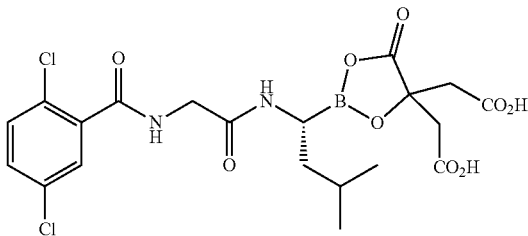

(IIIa)

or a pharmaceutically acceptable salt thereof, on days 1, 8 and 15 of a 28-day cycle,
wherein the patient is determined to also have at least one other cytogenetic alteration wherein the at least one other cytogenetic alteration is t(4:14) and/or t(14:16).

2. The method of claim 1, wherein the deletion at chromosome 17 is del (17p13).

3. The method of claim 1, wherein the at least one other cytogenetic alteration is t(4:14).

4. The method of claim 1, wherein the at least one other cytogenetic alteration is t(14:16).

5. The method of claim 1, wherein the patient is determined to have at least two other cytogenetic alterations wherein the at least two other cytogenetic alterations are t(4:14) and t(14:16).

6. The method of claim 1, wherein the determining that a patient has a cytogenetic alteration at chromosome 17 comprises the steps of:
   (i) providing a bone marrow aspirate sample from the patient;
   (ii) isolating CD138 positive plasma cells from the sample; and
   (iii) performing FISH analysis on the CD138 enriched positive plasma cells.

7. The method of claim 1, wherein the compound of formula (IIIa) is in a solid dosage form and the solid dosage form is a capsule.

8. The method of claim 7, wherein the capsule comprises a mixture of the compound of formula (IIIa) or a pharmaceutically acceptable salt thereof, microcrystalline cellulose, talc, and magnesium stearate.

9. The method of claim 1, wherein the treatment regimen further comprises lenalidomide and dexamethasone.

10. A method of treating a patient having multiple myeloma, comprising:
   i) selecting a patient based upon the patient having a cytogenetic alteration at chromosome 17, wherein the cytogenetic alteration at chromosome 17 is del (17); and
   ii) administering to the patient a treatment regimen comprising a compound of formula (IIIa):

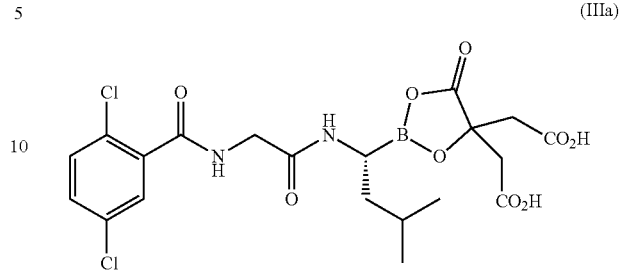

(IIIa)

or a pharmaceutically acceptable salt thereof,
wherein the patient is determined to also have at least one other cytogenetic alteration wherein the at least one other cytogenetic alteration is t(4:14) and/or t(14:16).

11. The method of claim 10, wherein the deletion at chromosome 17 is del (17p13).

12. The method of claim 10, wherein the at least one other cytogenetic alteration is t(4:14).

13. The method of claim 10, wherein the at least one other cytogenetic alteration is t(14:16).

14. The method of claim 10, wherein the patient is determined to have at least two other cytogenetic alterations wherein the at least two other cytogenetic alterations are t(4:14) and t(14:16).

15. The method of claim 10, wherein the selecting a patient based upon the patient having a cytogenetic alteration at chromosome 17 comprises the steps of:
   (i) providing a bone marrow aspirate sample from the patient;
   (ii) isolating CD138 positive plasma cells from the sample; and
   (iii) performing FISH analysis on the CD138 enriched positive plasma cells.

16. The method of claim 10, wherein the compound of formula (IIIa) is in a solid dosage form and the solid dosage form is a capsule.

17. The method of claim 16, wherein the capsule comprises a mixture of the compound of formula (IIIa) or a pharmaceutically acceptable salt thereof, microcrystalline cellulose, talc, and magnesium stearate.

18. The method of claim 10, wherein the compound of formula (IIIa) is administered on each of days 1, 8 and 15 of a 28 day cycle.

19. The method of claim 10, wherein the treatment regimen further comprises lenalidomide and dexamethasone.

* * * * *